United States Patent [19]

Scholz et al.

[11] Patent Number: 5,244,997
[45] Date of Patent: Sep. 14, 1993

[54] CATALYSTS, CATALYSIS METHOD, CASTING ARTICLE, AND METHOD OF ORTHOPEDIC CASTING

[75] Inventors: Matthew T. Scholz, Woodbury; Robert A. Scherrer, White Bear Lake, both of Minn.

[73] Assignee: Minnesota Mining and Manufacturing Company, St. Paul, Minn.

[21] Appl. No.: 941,765

[22] Filed: Sep. 4, 1992

Related U.S. Application Data

[62] Division of Ser. No. 742,048, Aug. 8, 1991, abandoned.

[51] Int. Cl.$^5$ ............................................. C08G 18/20
[52] U.S. Cl. .......................................... 602/6; 528/53
[58] Field of Search .............................. 528/53; 128/90

[56] References Cited

U.S. PATENT DOCUMENTS

| | | | |
|---|---|---|---|
| 2,934,538 | 4/1960 | Mizzoni | 548/569 |
| 2,980,673 | 4/1961 | Hidalgo | 548/569 |
| 3,821,131 | 6/1974 | Priest et al. | 260/2.5 |
| 4,376,438 | 3/1983 | Straube et al. | |
| 4,411,262 | 10/1983 | von Bonin | |
| 4,433,680 | 2/1984 | Yoon | |
| 4,502,479 | 3/1985 | Garwood | |
| 4,667,661 | 5/1987 | Scholz et al. | |
| 4,705,840 | 11/1987 | Buckanin | |

FOREIGN PATENT DOCUMENTS

| | | |
|---|---|---|
| 569284 | 1/1959 | Canada |
| 0407056 | 1/1991 | European Pat. Off. |
| 3134592 | 3/1983 | Fed. Rep. of Germany |
| 2207949 | 6/1974 | France |

OTHER PUBLICATIONS

Patent Abstracts of Japan, 28 Jun. 1991 and JP-30 84 021 (Mitsui Toatsu) 9 Apr. 1991.

*Primary Examiner*—Maurice J. Welsh
*Attorney, Agent, or Firm*—Gary L. Griswold; Walter N. Kirn; F. Andrew Ubel

[57] ABSTRACT

Amino-ester catalysts for curing water-curable isocyanate-functional materials. Also disclosed are catalysis methods and curable compositions involving amino-ester catalysts, and casting articles and methods of orthopedic casting.

7 Claims, No Drawings

CATALYSTS, CATALYSIS METHOD, CASTING ARTICLE, AND METHOD OF ORTHOPEDIC CASTING

This is a division of application Ser. No. 07/742,048 filed Aug. 8, 1991, now abandoned.

FIELD OF THE INVENTION

This invention relates to catalysts for curing isocyanate-functional materials. In another aspect, this invention relates to curable compositions comprising an isocyanate-functional material and a catalyst. This invention also relates to casting articles and methods of orthopedic casting.

BACKGROUND OF THE INVENTION

Orthopedic casts for use in treating bone fractures or other conditions requiring immobilization of a body member are generally formed from a sheet of fabric or scrim material coasted or impregnated with a substance that hardens into a rigid structure after the sheet has been wrapped around the body member.

Many orthopedic casts now commonly used are comprised of a backing impregnated with a water-curable isocyanate-functional prepolymer. The backing can be a knitted, woven, or nonwoven scrim comprised of natural, polymeric, or glass fibers. The preferred scrim materials are knitted fiberglass scrims. These casts when cured have a higher strength to weight ratio than plaster-of-paris, are more resistant to water and provide good radiolucency.

U.S. Pat. No. 4,411,262 (von Bonin), U.S. Pat. No. 4,502,479 (Garwood), and U.S. Pat. No. 4,667,661 (Scholz, et al.) disclose water-curable isocyanate-functional prepolymers useful in orthopedic bandages. The prepolymer typically includes a tertiary amine catalyst in an amount selected to optimize the "set" time. After the resin-impregnated scrim has been immersed in water, sufficient "working time", e.g., 3 to 5 minutes, should be provided in which the wrapping is accomplished and the cast is manually molded into a desired shape. However, after the cast is shaped, the resin should continue to harden and rapidly build strength, typically in 15-30 minutes, into a rigid, high-strength, weight-bearing cast.

U.S. Pat. No. 4,376,438 (Straube et al.) discloses an orthopedic casting material wherein the tertiary amine catalyst is incorporated into the backbone of the polymer portion of the isocyanate-functional prepolymer. No separate catalyst is required U.S. Pat. No. 4,502,479 (Garwood et al.) discloses the use of tertiary alkanolamines, e.g., dimethylethanolamine, as catalysts in the curing of a water-curable isocyanate-functional prepolymer. At concentrations that do not adversely affect shelf stability, these catalysts do not cure as fast as desired by many experienced cast appliers.

U.S. Pat. No. 4,433,680 (Yoon) discloses the use of 2,2'-dimorpholinodiethyl ether (DMDEE) as a catalyst in the cure of a water-curable isocyanate-functional prepolymer on an open-weave fibrous substrate to form an orthopedic bandage.

U.S. Pat. No. 4,705,840 (Buckanin) discloses the use of 2,2'-dimorpholinyldialkyl ethers substituted on one of the carbon atoms alpha to the central ether oxygen atom as catalysts in the curing of water-curable isocyanate-functional prepolymers.

SUMMARY OF THE INVENTION

This invention provides compounds of Formula I:

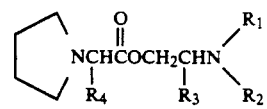

wherein: $R_1$ and $R_2$ are independently straight chain, branched chain, or cyclic alkyl of one to about six carbon atoms, or $R_1$ and $R_2$ together form a straight chain or branched chain alkylene group having four or five carbons in the main alkylene chain, or $R_1$ and $R_2$ together form a group of the formula -A-O-B- or

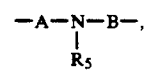

wherein
  A and B are independently straight chain or branched chain alkylene groups each having two carbon atoms in their main alkylene chain and $R_5$ is alkyl, aryl, or a deactivating substituent;
  $R_3$ is hydrogen or straight chain, branched chain, or cyclic alkyl of one to about six carbon atoms, or $R_1$ and $R_3$ together form a straight chain or branched chain alkylene group having three or four carbon atoms in the main alkylene chain, with the proviso that when $R_1$ and $R_3$ together form a straight chain or branched chain alkylene group having three or four carbon atoms in the main alkylene chain, then $R_2$ is straight chain, branched chain, or cyclic alkyl of one to about six carbon atoms; and $R_4$ is hydrogen, straight chain, branched chain, or cyclic alkyl of one to about six carbon atoms.

This invention also provides curable compositions comprising an isocyanate-functional prepolymer and a compound of Formula I in an amount effective to catalyze the cure of the prepolymer. This invention also provides casting articles comprising a flexible sheet with a coating of the above-described curable composition thereon. Further, this invention provides a catalysis method of catalysing the cure of a water-curable isocyanate-functional prepolymer comprising forming a mixture of:
  a) an isocyanate-functional material,
  b) water, and
  c) a catalytically effective amount of a compound of Formula I.

The use of the preferred compounds of Formula I as catalysts affords water-curable compositions having equivalent set times, better shelf stability and, when curing is initiated, affords materials having surprisingly superior early strengths when compared to compositions comprising commonly used catalysts of the prior art. The compositions of the invention are useful as adhesives, coatings, and sealants, and as the curable component of an orthopedic bandage.

DETAILED DESCRIPTION OF THE INVENTION

The compounds of the invention are compounds of Formula I, wherein $R_1$, $R_2$, $R_3$, $R_4$, $R_5$, A, and B are as defined above. $R_1$ and $R_2$ can be independently straight chain, branched chain, or cyclic alkyl of one to about six carbon atoms. $R_3$ can be hydrogen or straight chain, branched chain, or cyclic alkyl of one to about six carbon atoms Alternatively, $R_1$ and $R_2$ along with the catenary nitrogen therebetween can form a pyrrolidine ring or a piperidine ring.

When $R_1$ and $R_2$ together form a group of the formula -A-O-B- or $$-A-N-B-,$$
$$\phantom{-A-N}|\phantom{B-,}$$
$$\phantom{-A-N}R_5$$

morpholine ring or an N'-substituted piperazine ring for example can be formed. The N'-substituent $R_5$ is preferably a deactivating substituent, i.e., a group that substantially reduces the basicity of the N' nitrogen. For example, alkylcarbonyl, arylcarbonyl, alkoxycarbonyl [—C(O)Oalkyl], dialkylaminocarbonyl [—C(O)N(alkyl)$_2$], alkylaminocarbonyl, arylaminocarbonyl, alkylarylaminocarbonyl, and the like are suitable and others are easily selected by those skilled in the art. $R_5$ can also be an aryl group such as phenyl, naphthyl, and the like, including substituted aryl such as methylphenyl (i.e., tolyl) and methylnaphthyl. When $R_5$ is alkyl the number of carbons in the alkyl group is not unduly critical to the utility of the compounds as catalysts.

As a further alternative, $R_1$ and $R_3$ together can form a straight chain or branched chain alkylene chain having three or four carbons in the main alkylene chain, i.e., $R_1$ and $R_3$ along with the catenary nitrogen and the methine carbon therebetween can form a pyrrolidine or piperidine ring. In an instance wherein $R_1$ and $R_3$ form a pyrrolidine or piperidine ring, $R_2$ is straight chain, branched chain, or cyclic alkyl of one to about six carbon atoms (i.e., the ring is an N-alkyl pyrrolidine or piperidine ring).

Preferred compounds of the invention include: 2-(1-piperidino)ethyl 1-pyrrolidineacetate; 2-(4-morpholino)ethyl 1-pyrrolidineacetate; 2-(N,N-diethylamino)ethyl 1-pyrrolidineacetate; 2-(N,N-dimethylamino)ethyl 1-pyrrolidineacetate; and 2-(1-methylpiperidyl)methyl 1-pyrrolidineacetate. Most preferred is 2-(1-pyrrolidino)ethyl 1-pyrrolidineacetate. These compounds are preferred because, when combined with an isocyanate-functional prepolymer, they provide resins with superior strength soon after curing is initiated when compared with the commonly used catalysts of the prior art.

The compounds of this invention are 1-pyrrolidineacetates. They can be prepared by the transesterification reaction shown below, wherein the alkoxy portion of an ester of Formula II is replaced by the alkoxy portion of a compound of Formula III:

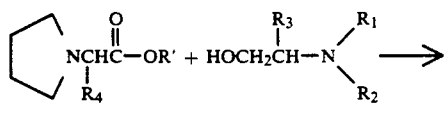

II  III

-continued

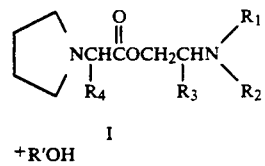

I

+R'OH and wherein $R_1$, $R_2$, $R_3$, and $R_4$ are as defined above, and "—OR'" designates an alkoxy, phenoxy, or other group capable of being displaced during the transesterification reaction.

The transesterification reaction can be carried out under conventional conditions, e.g., conditions involving such catalysts as dibutyl tin oxide, titanium isopropoxide, alkali metals, alkali metal hydrides and the like. Preferably the catalyst is sodium or potassium or the hydrides of these metals, because the residues of these catalysts are readily neutralized and separated from the product. Tin catalysts are less preferred, because the presence of tin compounds in an isocyanate-functional material can decrease the shelf stability of the material by catalyzing undesirable side reactions such as allophanate formation.

Synthetic intermediates of Formulas II and III are known, or can be readily prepared from other known compounds by methods well know to those skilled in the art. Compounds of Formula II, for example, are alkyl esters of either pyrrolidineacetic acid or 1-substituted pyrrolidineacetic acids. Such compounds can be prepared as described in the Examples below from alkyl α-haloalkanoates (wherein halo is bromo or chloro) by reaction with pyrrolidine. Compounds of Formula III are 2-(N,N-disubstituted amino)alkyl alcohols. These compounds are also generally known and can be prepared, for example, from the corresponding secondary amine and a suitable epoxide by methods well known to those skilled in the art.

The compounds of the invention are useful for curing any isocyanate-functional material or composition. They are particularly useful for curing water-curable isocyanate-functional prepolymers. In this regard it is notable that the compounds of the invention comprise an ester group and therefore would be expected to be relatively easily hydrolysed. Nonetheless, they function surprisingly well as catalysts of a reaction involving water.

Preferred prepolymers for use with the compounds of the invention are based on aromatic isocyanates. Such prepolymers are generally prepared by reacting a polyol with an excess of a polyisocyanate under conventional conditions. Such prepolymers are well known to those skilled in the art and are disclosed, e.g., in U.S. Pat. Nos. 4,411,262 (von Bonin et al.), 4,433,680 (Yoon), 4,502,479 (Garwood et al.), 4,667,661 (Scholz et al.), 4,705,840 (Buckanin), and 4,758,648 (Rizk et al.), the disclosures of each of which being incorporated herein by reference. A suitable prepolymer for use in a curable composition uses an isocyanate known as ISONATE ™ 2143L isocyanate (a mixture containing about 73% of diphenylmethane-4,4'-diisocyanate, Dow) and a polypropylene oxide polyol known as NIAX ™ PPG 725 (AC West Virginia Polyol Co.). To prolong the shelf-life of the material, it is preferred to include about 0.02-0.5 percent by weight of benzoyl chloride or other suitable stabilizer. The most preferred curable compositions, casting articles, catalysis methods, and orthopedic casting methods of the invention involve prepolymers described in co-pending, commonly assigned U.S. patent application Ser. No. 07/376,421, filed Jul. 7, 1989, entitled "Curable Resins With Reduced Foaming Characteristics And Articles Incorporating Same", the disclosure of which is incorporated herein by reference.

The compounds of Formula I are useful in curable compositions comprising an isocyanate-functional material and a catalytically effective amount of a compound of Formula I. As used herein, the term an "effective amount" designates an amount of a component sufficient to provide the desired physical properties (e.g., cure rate, set time, layer to layer lamination, and strength) to the curable composition. The particular amount of compound that constitutes a catalytically effective amount will vary with the particular compound used, the particular isocyanate-functional material used, the particular application of the curable composition, and the set time that is desired for the curable composition. Particular amounts are easily selected by those skilled in the art and are set forth generally below with respect to particular applications.

In order to prepare a curable composition, an isocyanate-functional material and a compound of Formula I can be mixed using conventional mixing techniques. In order to avoid premature curing of the resulting curable composition, the mixing should be done under anhydrous conditions, preferably in a substantially inert atmosphere, e.g., nitrogen gas. The resulting curable composition should also be stored under anhydrous conditions in a container substantially impermeable to oxygen and water vapor.

The curable compositions can be cured by exposure to water, e.g., water vapor or liquid water. For sealants, adhesives, and coatings, ordinary ambient humidity is usually adequate to promote cure. Heat or high humidity will accelerate cure, and low temperatures (e.g., 5° C. or less) or low humidity (e.g., 15% relative humidity or less) will retard cure. Bonds to damp substrates (e.g., wood) typically cure faster than bonds to dry substrates (e.g., glass). The reactivity of a curable composition once it is exposed to water as a curing agent can be controlled by the amount of compound of Formula I present in the curable composition. An effective amount of the compound is the amount necessary to achieve the desired reactivity.

One of the most advantageous uses of the compounds of this invention is in orthopedic casting applications, where a curable composition is used as the resin component of a resin-coated flexible sheet, which resin component hardens on exposure to water. (As used herein, the term "coating" is intended to designate not only a surface application of a composition, but also an application wherein a sheet material is impregnated with a composition, i.e., wherein the composition surrounds the fibers of the sheet material, or wherein the composition is absorbed by the fibers.)

For use in orthopedic casting, the reactivity of the curable composition must not be so great that: (1) a hard film quickly forms on the surface of the composition preventing further penetration of the water into the bulk of the composition; or (2) the cast becomes rigid before the application and shaping is complete. The particular preferred amount of compound of Formula I will depend upon the nature of the isocyanate-functional material, the desired set time, and the curing conditions. When the material is an isocyanate-functional polyurethane prepolymer based on an aromatic isocyanate, the amount of compound of Formula I suitable for orthopedic casting applications will generally range from about 0.1% to about by weight of the isocyanate-functional prepolymer, preferably from about 0.1 to about 3%, most preferably from about 0.5 to about 2%.

Foaming of the composition is preferably minimized because foaming reduces the porosity of the cast and its overall strength. Foaming occurs because carbon dioxide is released when water reacts with isocyanato groups. One way to minimize foaming is to add a foam suppresser such as ANTIFOAM ™ A silicone fluid (Dow Corning), ANTIFOAM ™ 1400 silicone fluid (Dow Corning), or L550 or L5303 silicone surfactants (Union Carbide). It is preferred to use a silicone liquid such as Dow Corning ANTIFOAM ™ 1400 silicone fluid at a concentration of about 0.1 to 1.0 percent by weight Casting articles, useful as orthopedic casting tapes, comprise a flexible sheet material with a water-curable composition coated thereon. They are preferably prepared by forming an isocyanate-functional prepolymer in the presence of a compound of Formula I as described above and coating the resulting curable composition onto a flexible sheet material, e.g., a fabric.

In the preferred embodiments relating to casting articles, a porous, flexible sheet material is used. The porous material is preferably impregnated with the composition. A preferred example of a porous, flexible sheet material that can be impregnated with the compositions of this invention is disclosed in U.S. Pat. No. 4,502,479. The sheet material disclosed therein imparts high structural strength to an orthopedic bandage prepared therefrom. A particularly preferred sheet material for use in casting articles is the scrim component of SCOTCHCAST ™ 2 Casting Tape (3M), disclosed as Example 1 of U.S. Pat. No. 4,609,578. The sheet material is a fiberglass fabric comprised of extensible knit fiberglass that exhibits an extensibility of at least about 20% in the length direction and has been heat set without tension in order to reduce fraying.

The amount of composition applied to the sheet material for use in a casting article such as an orthopedic casting tape must be sufficient for formation of a strong interlayer laminate bond but not so great as to occlude the porosity and unnecessarily thicken the sheet material, which should be thin for rapid and complete hardening. Excessive composition can also cause the casting article to be messy to handle because of stickiness or dripping and transfer of composition.

The sheet material used in a casting article (e.g., an orthopedic casting tape) is generally formed in rolls of various widths, generally from 2.5 cm (one inch) to 15 cm (six inches) wide. The sheet material can be coated with the curable composition in an amount, in terms of weight, of about 50 to about 500 g/m$^2$. In a preferred embodiment using a fiberglass fabric the curable composition preferably constitutes about 35% to about 50% by weight of the coated casting article. Generally, the composition will flow into the capillary spaces between contiguous filaments of the sheet material and will become rigidly bonded upon curing.

A casting article can be in the form of a roll wound up on a plastic core or in the form of a rolled or folded multi-layer laminate splint. The article can be sealed within a moisture- and oxygen-impermeable container such as an aluminum foil pouch. For use, the container is opened and the article is fully immersed and squeezed in tap water for about 5 to 30 seconds to replace entrapped air with water. Generally a sufficient amount of water is absorbed by the article in this manner. When a roll is unwound during wrapping of a cast, the excess moisture coats the freshly exposed composition surfaces insuring thorough wetting and rapid hardening. An alternate but less preferable method involves wrapping the cast without dipping and then allowing atmospheric moisture or water provided by spraying or by application of a wet towel to cure the composition.

Prior to applying an orthopedic cast to a limb or body member of a patient, a protective layer can be positioned about the limb or body member. The protective layer can take the form of a tubular stockinet or some other convenient form such as, for example, an elongate, non-woven, cotton, or polyester strip or bandage that can be wrapped about the limb or body member.

With the protective layer in a proper position, the moistened or dry casting article can be wrapped about the body member and over the protective layer in a manner similar to that used in applying an elastic bandage. The cast can be shaped in a manner similar to that used in shaping a plaster-of-paris cast.

Eight or fewer layers of the cast material are generally sufficient to form a cast having significant strength within about 8 minutes and having weight-bearing strength within 30 minutes. A fully cured cylindrical laminate having eight or fewer layers, e.g., six layers, should support at least about 3.6 kg per cm (20 lb per inch) and preferably 7.2 kg/cm (40 lb/per inch) of cylinder length according to the dry strength ring strength test. The tests to determine these strengths are discussed more fully below.

DELAMINATION TEST

This test measures the force necessary to delaminate a cured cylinder of a resin-coated material.

Each cylinder ring is formed by removing a roll of 3 inch (7.62 cm) wide resin-coated material from its storage pouch and immersing the roll completely in deionized water having a temperature of about 80° F. (27° C.) for about 30 seconds. The roll of resin-coated material is then removed from the water and the material is wrapped around a 2 inch diameter (5.08 cm) mandrel covered with a thin stockinet to form six complete uniform layers using a controlled wrapping tension of about 45 grams per centimeter width of the material. A free tail about 6 inches (15.24 cm) long is kept and the rest of the roll is cut off. Each cylinder is completely wound within 30 seconds after removal of the roll from the water.

Fifteen to 20 minutes after initial immersion of the roll in water, the cured cylinder is removed from the mandrel. Delamination strength is determined as follows:

The free tail of the cylinder is placed in the jaws of an INSTRON ™ Model 1122 tensile testing machine and a spindle is placed through the hollow core of the cylinder so that the cylinder rotates freely about the axis of the spindle. The tensile testing machine is then activated to pull on the free tail at a speed of 127 cm/min. The average force required to delaminate the wrapped layers over the first 33 centimeters of the material is recorded in terms of force per unit width of sample (newtons/cm). For each material, at least five samples are tested, and the average delamination force is calculated and reported as the "delamination strength."

RING STRENGTH TESTS

In these tests, the "dry strength", "wet strength", and "warm wet strength", of cured cylinders of resin-coated materials are determined. For each of these tests, cured cylinders are formed as described above in connection with the delamination test so as to form six-layered cylinders around a 2 inch (5.08 cm) mandrel. All excess material is trimmed off, leaving no tails.

Thirty minutes after initial immersion in water, each cylinder is removed from its respective mandrel and allowed to cure for 48–60 hours in a controlled atmosphere of 75° F. ± 3° F. (34° C. ± 2° C) and 55% ±5% relative humidity. Each cylinder is then placed in the fixture of an INSTRON ™ tensile testing machine. Compression loads are applied to the cylinder along its exterior and parallel to its axis. The cylinder is placed lengthwise between the two bottom bars of the fixture (the bars being 1.9 centimeters wide, 1.3 centimeters in height, and 15.2 centimeters long, and spaced about 4 centimeters apart). The inside edges of the bars have a curved surface having a ⅛ inch (0.31 cm) radius. A third bar (0.63 cm wide, 2.5 cm high, and 15.2 cm long) is then centered over the top of the cylinder, parallel to its axis. The contacting (bottom) edge of the third bar has a curved surface having a ⅛ inch (0.31 cm) radius. The third bar is brought down to bear against and crush the cylinder at a speed of about 5 cm/min. The maximum or peak force applied while crushing the cylinder is recorded as the ring strength, which in this particular instance is the "dry strength" (expressed in terms of force per unit length of the cylinder, i.e., newtons/cm). For each material, at least five samples are tested, and the average peak force applied is calculated and reported as the "dry strength."

To measure the "wet strength", the same procedure is followed as for the "dry strength", except that after curing for 48–60 hours, the cylinder is immersed in water at about 113° F. (45° C.) for about 30 minutes, and then allowed to dry under ambient conditions for about 15 minutes. The cylinder is then placed in the instrument and crushed as described above in order to determine "wet strength."

To determine the "warm wet strength" of the cylinder, the procedure as set forth above for "wet strength" is followed, except that the cylinder is placed in the fixture and crushed immediately after removal from the 113° F. (45° C.) water bath.

In addition to the above-described use in orthopedic casting, curable compositions comprising an isocyanate-functional material and a compound of Formula I will be useful in a variety of applications wherein isocyanate-functional materials have been used previously, e.g., as sealants (e.g., caulks), coatings, foams, adhesives, and so forth. They can be applied to a variety of articles and substrates, such as articles or substrates of glass, metal, plastic, wood, leather, masonry, textiles, and the like.

When used as an adhesive, the composition is placed between an article and a substrate, in contact with both, and exposed to moisture sufficient to cure the composition. When used as a coating, the composition is deposited as a continuous layer on the surface of the article to be coated and exposed to moisture sufficient to cure the composition. When used as a sealant, the composition is deposited in the void to be sealed and exposed to moisture sufficient to cure the composition. When used as a structural reinforcing material, the composition is coated onto and/or impregnated into an article comprised of a flexible sheet of fibrous or non-fibrous fabric, paper, felt, foam or the like and exposed to moisture sufficient to cure the composition. When used for making foams the composition is generally mixed with a precise amount of water and is subsequently poured into an appropriate mold. For such applications wherein the isocyanate-functional material is an isocyanate-functional polyurethane prepolymer based on an aromatic isocyanate, an effective amount of amino-ester catalyst preferably is about 0.002 to 2 weight percent, and most preferably about 0.05 to 0.5 weight percent based upon the weight of prepolymer.

Other ingredients and adjuvants can be incorporated into the compositions of the invention. Suitable ingredients and adjuvants and effective amounts thereof are disclosed, e.g., in U.S. Pat. No. 4,705,840 (Buckanin) and are easily selected by those skilled in the art.

Curable compositions of the invention can be put into packages according to techniques known to those skilled in the art. Suitable packages include, for example, aluminum foil laminate pouches, caulking tubes (made, for example, of aluminum foil laminates, metal, or plastic), screw-capped squeezable tubes, cans, drums, and the like.

The following Examples are provided to illustrate the invention and are not intended to limit the scope of the invention. Parts and percentages are by weight unless otherwise indicated, and temperatures are designated in degrees Celsius.

EXAMPLE 1. ETHYL 1-PYRROLIDINEACETATE

To an ice bath-cooled solution of 213.4 g (3 mol) of pyrrolidine in 450 mL of tetrahydrofuran was added dropwise over about 2 hours 250.5 g (1.5 mol) of ethyl bromoacetate, maintaining the temperature below 30° C. To this solution was added 150 mL of toluene to precipitate pyrrolidinium bromide, which was separated by filtration. The filtrate was evaporated under vacuum to provide a residue of about 241 g of ethyl 1-pyrrolinidineacetate.

EXAMPLE 2. 2-(1-PIPERIDINO)ETHYL 1-PYRROLIDINEACETATE

A mixture of 78.5 g (0.5 mol) of ethyl 1-pyrrolidineacetate, 64.6 g (0.5 mol) of 2-piperidinoethanol and 1.0 g of dibutyltin oxide was heated at about 150° C. while collecting the ethanol by-product in a Dean-Stark trap. When the rate of ethanol evolution and amount of ethanol collected showed that the reaction was essentially complete, the reaction was heated at about 170° C. until ethanol evolution ceased. The liquid product was purified by distillation at reduced pressure to provide 2-(1-piperidino)ethyl 1-pyrrolidineacetate.

EXAMPLE 3. 2-(4-MORPHOLINO)ETHYL 1-PYRROLIDINEACETATE

Using the method of Example 2, 75.5 g ethyl 1-pyrrolidineacetate was reacted with 65.6 g of 4-(2-hydroxyethyl)morpholine to provide the desired product, which was purified by distillation at a temperature of about 120° C and a pressure of about 300 μmHg.

EXAMPLE 4. 2-(N,N-DIMETHYLAMINO)ETHYL 1-PYRROLIDINEACETATE

To a mixture of 80 g (0.51 mol) of ethyl 1-pyrrolidineacetate and 0.5 g of sodium hydride (in the form of a 60% by weight suspension in mineral oil) was added 48 g (0.54 mol) of 2-(N,N-dimethylamino)ethanol. The mixture was purged with nitrogen gas, heated gradually and then maintained at about 150° C. while collecting the ethanol by-product in a Dean-Stark trap. The liquid reaction product was distilled at 85° C. at a pressure of 100 μmHg to provide 2-(N,N-dimethylamino)-ethyl 1-pyrrolidineacetate. The structure of the product was confirmed by nuclear magnetic resonance and infrared spectral analysis.

EXAMPLE 5. 2-(1-PYRROLIDINYL)ETHYL 1-PYRROLIDINEACETATE

To a mixture of 1.3 g of sodium hydride (in the form of a 60% by weight suspension in mineral oil) and 100 g (0.64 mol) of ethyl 1-pyrrolidineacetate was added 91 g of 2-(1-pyrrolidinyl)ethanol. The mixture was heated slowly to about 225° C., and the ethanol by-product was collected in a Dean-Stark trap. The reaction mixture was cooled to about 25° C., then 12 g of 1-bromopropane was added to react any alkoxide present. The sodium bromide by-product was removed by filtration. The desired product 2-(1-pyrrolidinyl)ethyl 1-pyrrolidineacetate was purified by distillation at 95° C. at a pressure of 250 μmHg. The structural assignment was confirmed by mass spectral analysis.

EXAMPLE 6. 2-(N,N-DIETHYLAMINO)ETHYL 1-PYRROLIDINEACETATE

Using the method of Example 5, ethyl 1-pyrrolidineacetate was reacted with 2-(N,N-diethylamino)ethanol to provide 2-(N,N-diethylamino)ethyl 1-pyrrolidineacetate, b.p. 92° C. at 250 μmHg.

EXAMPLE 7. 2-(1-Methylpiperidyl)methyl 1-Pyrrolidineacetate

Using the method of Example 5, ethyl 1-pyrrolidineacetate was reacted with 2-(1-methylpiperidyl)methanol to provide 2-(1-methylpiperidyl)methyl 1-pyrrolidineacetate. Purification was carried out by distillation at 125° C. and at a pressure of 400 μmHg.

EXAMPLE 8. N-(N-ACETYLPIPERAZINYL)ETHYL 1-PYRROLIDINEACETATE

Using the method of Example 4, 43.2 g of ethyl 1-pyrrolidineacetate was reacted with 42.5 g of N-(2-hydroxyethyl)-N'-acetylpiperazine in the presence of 0.7 g of 60 weight percent sodium hydride in mineral oil. The product was purified by distillation at a temperature of about 180° C and a pressure of about 0.5 mmHg. Gas chromatography of the product showed a single major constituent.

EXAMPLES 9-11

Curable compositions useful, for example, in connection with orthopedic casting materials, sealants, adhesives, foams, or coatings, comprising a compound of the invention were prepared and their gel times measured as set forth below:

To a stirred 30.00 g sample of ISONATE TM 2143L isocyanate (Dow) in a 100 mL (4.5 cm diameter) polyethylene beaker was added 0.30 g of a compound of Formula I, then 10 mL of water was added gently from a syringe. The mixture was stirred by hand with a 1.7 cm wide wooden tongue depressor at a rate of about 60 to 75 rpm. The time until gelation occurred was recorded as gel time. Gelation was defined as the point at which the viscosity was sufficient to allow formation of a permanent depression in the mixture.

The gel time was found to be 45 seconds for the composition of Example 9, comprising 2-(1-piperidino)ethyl 1-pyrrolidineacetate, 90 seconds for the composition of Example 10, comprising 2-(4-morpholino)ethyl 1-pyrrolidineacetate, and 400 seconds for the composition of Example 11, comprising for N-(N-acetylpiperazinyl)ethyl 1-pyrrolidineacetate

EXAMPLE 12

A further curable composition useful, for example, in connection with an orthopedic casting material, a sealant, an adhesive, a foam, or a coating, was prepared as follows:

An amount, 1125 g (7.76 equivalents), of ISONATE TM 2143L isocyanate (modified diphenylmethane diisocyanate, Dow) was added to a one gallon (4L) jar having a three-necked lid equipped with a thermometer, stirrer and nitrogen inlet. To this was added 29.99 g of the catalyst 2-(1-piperidino)ethyl 1-pyrrolidineacetate from Example 2, 1.0 g of para-toluenesulfonyl chloride, 80 g of PLURONIC TM F-108 polyethylene oxide-polypropylene oxide block copolymer (available from BASF Wyandotte Corporation), and 3.6 g of Dow-Corning DB-100 silicone fluid. This was followed by the addition of 9.6 g of BHT (2,6-di-tert-butyl-4-methylphenol) in 480 g of NIAX TM PPG-725 (a polypropylene oxide polyol having a molecular weight of about 750, AC West Virginia Polyol Co.) and 270 g of NIAX TM PPG-425 (a polypropylene oxide polyol having a molecular weight of about 425, AC West Virginia Polyol Co.). The addition of the polyol mixture was made through a dropping funnel over a period of thirty minutes. After addition the polymerization reaction was carried out at 50°–60° C. for one hour to afford a curable composition of the invention.

EXAMPLES 13-15 AND COMPARATIVE EXAMPLES C-1 THROUGH C-3

In the manner of Example 12 above, compounds of Formula I and known catalysts were independently incorporated into curable compositions as set forth in Table 1 below, wherein catalyst concentration is given in weight percent based on the total weight of the curable composition.

TABLE 1

| Example | Catalyst | Example Number | Concentration (%) |
|---|---|---|---|
| 13 | 2-(N,N-diethylamino)ethyl 1-pyrrolidineacetate | 6 | 0.9 |
| 14 | 2-(N,N-dimethylamino)ethyl 1-pyrrolidineacetate | 4 | 0.8 |
| 15 | 2-(1-pyrrolidinyl)ethyl 1-pyrrolidineacetate | 5 | 0.75 |
| C-1 | DMDEE TM (Texaco)[A] | — | 2.5 |
| C-2 | MEMPE[B] | — | 1.32 |
| C-3 | NIAX TM A-99[C]DMEA[D] | — | 0.3/0.3 |

[A] 2,2'-Dimorpholinodiethyl ether
[B] Morpholinoethyl morpholinoisopropyl ether
[C] [(CH₃)₂NCH₂CH₂]₂O, AC West Virginia Polyol Co.
[D] Dimethylethanolamine

EXAMPLES 16-17

Further curable compositions useful, for example, in connection with orthopedic casting materials, sealants, adhesives, foams, or coatings, were prepared according to the general method of Example 12 above. The particular catalyst used and the amount thereof in weight percent based on total weight of the composition are shown in Table 2. The amount of catalyst used was selected to provide a set time of approximately 3 minutes. About 2.5 to 3 kg of each composition was made, mixed for about 2 hours, and sealed in several 240 mL (8 oz) glass jars.

TABLE 2

| Example | Catalyst | Example Number | Concentration (%) |
|---|---|---|---|
| 16 | 2-(1-methylpiperidino)methyl 1-pyrrolidineacetate | 7 | 0.6 |
| 17 | 2-(N,N-dimethylamino)ethyl 1-pyrrolidineacetate | 4 | 0.9 |

AGING DATA

The compositions of each of Examples 13-15 and Comparative Examples C-1 through C-3 were independently machine coated using a curtain coating technique in an atmosphere substantially free of moisture (less than 5% relative humidity) on a 7.6 cm (three inch) wide strip of heat-set fiberglass fabric [the fabric of SCOTCHCAST PLUS TM casting tape, 3M, described in U.S. Pat. No. 4,609,578 (Reed)] to give a casting article in the form of a tape containing 42.5% by weight of the composition based on total weight of the tape. The tape was then cut in lengths of about 3.65 m (4 yards), rolled onto 7.6 cm (3 inch) long hollow cylindrical polyethylene cores having a diameter of 19 cm (0.75 inch), and packaged in foil pouches for storage until later use and evaluation. Rolled samples of the casting article prepared above were stored in sealed aluminum foil envelopes similar to those used to store similar commercial items. The casting articles were subjected to accelerated aging at a temperature of 65.5° C. (150° F.) for the period of time indicated in Table 3 below. After cooling to 23°–25° C. and equilibrating for 24 hours, the rolls were sequentially removed from the pouches and immediately unwound in such a manner that the force needed to unwind the rolls could be measured.

The force needed to unwind the rolls was measured using an Instron TM Model 1122 tensile testing machine with a 50lb (22.7 Kg) load cell. Each roll was unwound counterclockwise from a freely rotating spindle over a freely rotating crosshead spindle attached to the load cell of the tensile testing machine onto a 3.875 inch (9.84 cm) diameter take-up roller rotating at 60 revolutions per minute covered with stockinette (3M MS04). The crosshead spindle consisted of a freely rotating ⅜ inch dia × 5.5 inch (0.95cm × 14 cm) long rod counterbalanced to ensure that it hung in a horizontal position parallel to both the unwind spindle and the take-up roller. The force was measured by a Microcon TM Model MC4100 microprocessor using the following machine conditions:

Area = 0
gage length = 4.5 inches (11.4 cm)
crosshead speed = 0.1 inches/min (0.254cm/min)
Start force averaging at 0.0005 inches (0.00127cm) (preset point 8, elongation, 0.005)
End force averaging at 0.0136 inches (0.0345cm) (preset point 9, elongation, 0.0136)
Fail Criteria = 100%
Load Limit = 43,360 kg force
Crosshead stop = off
Elongation correction factor = no correction The average force over 95.7 inches (24.3 cm) of tape was recorded as the unwind force (ignoring the first 3.65 inches (9.3 cm) of tape).

The unwind force was measured for 5 rolls and the average values are set forth in TABLE 3 below, wherein a lack of an entry indicates that the roll was cured when tested.

TABLE 3

| | Unwind Force (Newtons) Example | | | | | |
|---|---|---|---|---|---|---|
| Day | 13 | 14 | 15 | C-1 | C-2 | C-3 |
| 0 | 6.85 | 6.05 | 6.41 | 5.6 | 8.76 | 8.81 |
| 7 | 11.0 | 9.46 | 10.1 | 8.65 | 11.0 | — |
| 16 | 20.3 | 37.7 | 18.6 | 13.6 | 15.8 | — |
| 24 | 48.1 | — | 38.6 | 19.8 | 27.5 | — |

The results in Table 3 show that upon accelerated aging these casting articles comprising a catalyst of this invention exhibit unwind tension comparable to, and often superior to, those of the comparative examples.

240 mL (8 oz) samples of the compositions of Examples 15-17 and Comparative Examples C-1 and C-2 above were subjected to accelerated aging conditions of 49° C. in sealed glass jars. Individual samples were periodically cooled to room temperature and then equilibrated for 2 hours in a water bath at 23° C. The viscosity of the cooled sample was measured using a SYNCHRO-LECTRIC TM Viscometer Model RVT (Brookfield Engineering Labs, Inc., Spoughton, Mass.) using spindles #6 and #7. The viscosities are set forth in Table 4 below.

TABLE 4

| | Viscosity (cps × $10^{-3}$) Example | | | | |
|---|---|---|---|---|---|
| Day | 15 | 16 | 17 | C-1 | C-2 |
| 0 | 75 | 72 | 69 | 66 | 58 |
| 7 | 80 | 74 | 81 | 86 | 58 |
| 14 | 120 | 96 | 98 | 88 | 72 |
| 21 | 138 | 96 | 106 | 90 | 72 |
| 28 | 204 | 124 | 130 | 108 | 78 |
| 35 | 300 | 152 | 170 | 120 | 82 |
| 42 | 470 | 150 | 232 | 116 | 80 |
| 49 | 590 | 208 | 266 | 128 | 72 |

PKA

Several of the compounds of the invention were characterized by their titration curves (i.e., their pKa values) as follows:

To a 0.1 g sample of a compound of the invention was added with stirring 60 mL of distilled water, then 10 mL of 0.1N hydrochloric acid was added. The solution was stirred for 10 minutes. The pH of the solution was then measured potentiometrically using a Metrohm Model 670 TITROPROCESSOR TM potentiometer (Brinkman Instruments Inc., Westbury, N.Y.) while backtitrating with 0.01N sodium hydroxide solution. The endpoints and half-neutralization points were determined by the instrument, and for the purposes of this determination the half-neutralization point is taken as the pKa. The values of pKa for several compounds are as shown in Table 5.

TABLE 5

| | Measured pKa | |
|---|---|---|
| Compound | first | second |
| 2-(1-piperidino)ethyl 1-pyrrolidineacetate | 8.97 | 6.72 |

TABLE 5-continued

| | Measured pKa | |
|---|---|---|
| Compound | first | second |
| 2-(1-pyrrolidino)ethyl 1-pyrrolidineacetate | 9.26 | 7.12 |
| 2-(1-methylpiperidinyl)methyl 1-pyrrolidineacetate | 9.15 | 7.03 |

EXAMPLE 18

A curable composition useful, for example, in connection with an orthopedic casting material, a sealant, an adhesive, a foam, or a coating, was prepared as follows:

An amount, 2210 g (15.35 equivalents), of ISONATE TM 2143L isocyanate (modified diphenylmethane diisocyanate, Dow) was added to a one gallon (4L) jar having a three-necked lid equipped with a thermometer, heating mantle, stirrer, and nitrogen inlet. To this was added 1.8 g of benzoyl chloride, 6.66 g of Dow-Corning DB-100 silicone fluid, 17.76 g of BHT (2,6-di-tert-butyl-4-methylphenol), 148 g of PLURONIC TM F-108 polyethylene oxide-polypropylene oxide block copolymer (available from BASF Wyandotte Corporation) and 22.2 g of 2-(1-methylpiperidyl)methyl 1-pyrrolidineacetate (Example 7). This was followed by the addition of 620.1 g of NIAX TM Polyol PPG-2025 (a polypropylene oxide polyol having a molecular weight of about 2025, available from AC West Virginia Polyol Co.), 229.4 g of LG 650 polyol (a polyol containing polymeric particles, available from AC West Virginia Polyol Co.), and 444 g of NIAX TM E-562 (a polypropylene oxide available from AC West Virginia Polyol Co.). The polymerization reaction was carried out at 50°-60° C. for one hour to afford a curable composition.

EXAMPLE 19 AND COMPARATIVE EXAMPLE C-4

Using the general method of Example 18, 2-(1-pyrrolidino)ethyl 1-pyrrolidineacetate (Example 5) was incorporated into the curable composition of Example 19. As Comparative Example C-4, a composition using MEMPE as a catalyst was prepared. The ingredients and amounts used in Example 19 and Comparative Example C-4 are shown in Table 6.

TABLE 6

| Component | Example 19 Weight (g) | Comparative Example C-4 Weight (g) |
|---|---|---|
| ISONATE TM 2143L | 2204.46 | 2183.9 |
| Benzoyl Chloride | 1.85 | 0 |
| p-Toluenesulfonyl Chloride | 0 | 1.8 |
| DB-100 | 6.66 | 66.6 |
| BHT | 17.75 | 17.75 |
| Catalyst | 27.75 | 48.81 |
| PLURONIC TM F-108 | 148.0 | 147.91 |
| NIAX TM PPG-2025 | 620.12 | 620.12 |
| LG 650 | 229.40 | 229.26 |
| NIAX TM E-562 | 444.00 | 443.74 |
| TOTAL | 3700.00 | 3700.00 |

The compositions of Examples 18 and 19 and Comparative Example C-4 were machine coated as described above in connection with "Aging Data". The resulting casting tapes were packaged in foil pouches for storage until later use and evaluation.

Using the tests described above, "dry strength", "wet strength", "ring delamination", and "warm wet strength" were measured for casting tapes comprising Compositions 18 and 19 and Comparative Composition C-4. The results are shown in Table 7 below:

TABLE 7

| Strength Test | Example 18 | Example 19 | C-4 |
|---|---|---|---|
| Dry | 911.9 | 900.8 | 863.8 |
| Wet | 696.6 | 703.7 | 492 |
| Warm Wet | 528.4 | 524.9 | 285.1 |
| Ring Delamination | 56.5 | 53.4 | 51.2 |

(Strength measured in newtons)

The results in Table 7 show that, when used in curable compositions and casting tapes, compounds of this invention provide useful products that exhibit significantly higher wet strength, warm wet strength, and ring delamination values than the Comparative Example.

What is claimed is:

1. A curable composition comprising (i) an isocyanate-functional material; and (ii) a catalytically effective amount of a compound of the formula

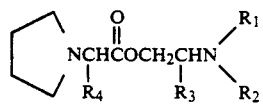

wherein
$R_1$ and $R_2$ are independently straight chain, branched chain, or cyclic alkyl of one to about six carbon atoms, or $R_1$ and $R_2$ together form a straight chain or branched chain alkylene group having four or five carbons in the main alkylene chain, or $R_1$ and $R_2$ together form a group of the formula -A-O-B- or

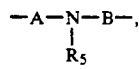

wherein A and B are independently straight chain or branched chain alkylene groups each having two carbon atoms in their main alkylene chain and $R_5$ is alkyl, aryl, or a deactivating substituent; $R_3$ is hydrogen or straight chain, branched chain, or cyclic alkyl of one to about six carbon atoms, or $R_1$ and $R_3$ together form a straight chain or branched chain alkylene group having three or four carbon atoms in the main alkylene chain, with the proviso that when $R_1$ and $R_3$ together form a straight chain or branched chain alkylene group having three or four carbon atoms in the main alkylene chain, then $R_2$ is straight chain, branched chain, or cyclic alkyl of one to about six carbon atoms; and $R_4$ is hydrogen, straight chain, branched chain, or cyclic alkyl of one to about six carbon atoms.

2. A curable composition according to claim 1, wherein the isocyanate-functional material is an isocyanate-functional prepolymer based on an aromatic isocyanate.

3. An article comprising a flexible sheet material coated with a composition according to claim 1.

4. An article according to claim 3 in the form of an orthopedic casting tape.

5. A catalysis method for catalysing the cure of an isocyanate-functional material comprising forming a mixture of:
   a) an isocyanate-functional material,
   b) water, and
   c) a catalytically effective amount of a compound of the formula

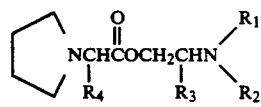

wherein
$R_1$ and $R_2$ are independently straight chain, branched chain, or cyclic alkyl of one to about six carbon atoms, or $R_1$ and $R_2$ together form a straight chain or branched chain alkylene group having four or five carbons in the main alkylene chain, or $R_1$ and $R_2$ together form a group of the formula -A-O-B- or

wherein A and B are independently straight chain or branched chain alkylene groups each having two carbon atoms in their main alkylene chain and $R_5$ is alkyl, aryl, or a deactivating substituent;
$R_3$ is hydrogen or straight chain, branched chain, or cyclic alkyl of one to about six carbon atoms, or $R_1$ and $R_3$ together form a straight chain or branched chain alkylene group having three or four carbon atoms in the main alkylene chain, with the proviso that when $R_1$ and $R_3$ together form a straight chain or branched chain alkylene group having three or four carbon atoms in the main alkylene chain, then $R_2$ is straight chain, branched chain, or cyclic alkyl of one to about six carbon atoms; and $R_4$ is hydrogen, straight chain, branched chain, or cyclic alkyl of one to about six carbon atoms.

6. A method according to claim 5, wherein the isocyanate-functional material is an isocyanate-functional prepolymer based on an aromatic isocyanate.

7. A method of orthopedic casting comprising the steps of:
   (i) providing a flexible sheet material coated with a composition according to claim 1;
   (ii) contacting the coated sheet material with water in order to initiate curing of the composition; and
   (iii) applying the coated sheet material to a body member of a subject.

* * * * *

UNITED STATES PATENT AND TRADEMARK OFFICE
CERTIFICATE OF CORRECTION

PATENT NO. : 5,244,997
DATED : September 14, 1993
INVENTOR(S) : Matthew T. Scholz and Robert A. Scherrer It is certified that error appears in the above-indentified patent and that said Letters Patent is hereby corrected as shown below:

Col. 1, line 21, "coasted" should be -- coated --.

Col. 3, line 14, insert -- a -- before "morpholine".

Col. 10, line 8, "1" should not be boldface.

Col. 10, line 39, "1" (first instance) should not be boldface.

Col. 11, line 9, insert a period -- . -- at the end of the sentence.

Col. 12, line 30, "19 cm" should be -- 1.9 cm --.

Col. 14, line 41, "1" should not be boldface.

Col. 14, Table 6, In the column under "Example 19", after the "Component BHT", "17.75" should be -- 17.76 --.

Signed and Sealed this

Twenty-third Day of August, 1994

Attest:

BRUCE LEHMAN

Attesting Officer

Commissioner of Patents and Trademarks